(12) United States Patent
Nevo et al.

(10) Patent No.: US 9,161,815 B2
(45) Date of Patent: Oct. 20, 2015

(54) DERMATOLOGICAL LASER SYSTEM AND METHOD FOR SKIN RESURFACING

(75) Inventors: Doron Nevo, Ra'anana (IL); Ram Oron, Rehovot (IL); Peter McIlroy, Ottawa (CA); Moshe Oron, Rehovot (IL)

(73) Assignee: KiloLambda Technologies Ltd., Tel-Aviv (IL)

( * ) Notice: Subject to any disclaimer, the term of this patent is extended or adjusted under 35 U.S.C. 154(b) by 2163 days.

(21) Appl. No.: 11/629,230

(22) PCT Filed: Jun. 20, 2005

(86) PCT No.: PCT/IB2005/001736
§ 371 (c)(1),
(2), (4) Date: Dec. 11, 2006

(87) PCT Pub. No.: WO2006/000873
PCT Pub. Date: Jan. 5, 2006

(65) Prior Publication Data
US 2007/0179480 A1      Aug. 2, 2007

Related U.S. Application Data

(60) Provisional application No. 60/581,395, filed on Jun. 21, 2004, provisional application No. 60/686,907, filed on Jun. 2, 2005.

(51) Int. Cl.
*A61B 19/00* (2006.01)
*A61B 18/18* (2006.01)
*A61B 18/22* (2006.01)
*A61B 18/20* (2006.01)
*A61B 18/00* (2006.01)

(52) U.S. Cl.
CPC .............. *A61B 18/22* (2013.01); *A61B 18/203* (2013.01); *A61B 2018/00452* (2013.01); *A61B 2018/2085* (2013.01); *A61B 2018/2211* (2013.01)

(58) Field of Classification Search
CPC ........ A61B 18/18; A61B 18/20; A61B 18/22; A61B 19/00
USPC .................. 606/3, 9, 10; 607/88, 89; 128/898
See application file for complete search history.

(56) References Cited

U.S. PATENT DOCUMENTS

| 5,336,217 A | 8/1994 | Buys et al. |
| 5,879,346 A * | 3/1999 | Waldman et al. ................. 606/9 |
| 5,964,749 A | 10/1999 | Eckhouse et al. |

(Continued)

FOREIGN PATENT DOCUMENTS

WO        2004/107510        12/2004

OTHER PUBLICATIONS

International Search Report for International Application No. PCT/IB05/01736, dated Jan. 31, 2006, 1 page.

(Continued)

*Primary Examiner* — Ahmed Farah
(74) *Attorney, Agent, or Firm* — Nixon Peabody LLP (57) ABSTRACT

A dermatological laser apparatus for irradiating human tissue with optical pulses includes a laser source (2) producing an optical output, a pulse shaper (4) coupled to the laser source for converting the optical output into optical pulses having desired shapes, and an optical delivery tool (8) coupled to the pulse shaper for applying the optical pulses sequentially to a multiplicity of sites on the human tissue with consecutively irradiated sites being non-adjacent.

11 Claims, 8 Drawing Sheets

(56) References Cited

U.S. PATENT DOCUMENTS

| | | | |
|---|---|---|---|
| 6,120,497 | A | 9/2000 | Anderson et al. |
| 6,171,301 | B1 | 1/2001 | Nelson et al. |
| 6,273,885 | B1 | 8/2001 | Koop et al. |
| 6,451,007 | B1 | 9/2002 | Koop et al. |
| 6,610,052 | B2 * | 8/2003 | Furumoto ............ 606/9 |
| 6,676,655 | B2 * | 1/2004 | McDaniel ............ 606/9 |
| 6,695,835 | B2 * | 2/2004 | Furuno et al. ....... 606/9 |
| 7,090,670 | B2 * | 8/2006 | Sink .................... 606/9 |
| 7,413,572 | B2 * | 8/2008 | Eimerl et al. ........ 607/88 |
| 7,926,490 | B2 * | 4/2011 | Dai et al. ............. 128/898 |
| 2001/0016732 | A1 | 8/2001 | Hobart et al. |
| 2001/0034517 | A1 | 10/2001 | Masotti et al. |
| 2002/0002391 | A1 | 1/2002 | Gerdes |
| 2002/0016587 | A1 | 2/2002 | Furumoto |
| 2002/0049432 | A1 | 4/2002 | Mukai |
| 2002/0049433 | A1 | 4/2002 | Furumoto et al. |
| 2002/0058953 | A1 | 5/2002 | Gruzdev et al. |
| 2002/0077678 | A1 | 6/2002 | Andersen et al. |
| 2002/0111656 | A1 | 8/2002 | Lach |
| 2002/0120256 | A1 | 8/2002 | Furuno et al. |
| 2002/0120315 | A1 | 8/2002 | Furuno et al. |
| 2004/0010300 | A1 | 1/2004 | Masotti et al. |
| 2004/0082940 | A1 | 4/2004 | Black et al. |
| 2004/0082941 | A1 | 4/2004 | Connors et al. |
| 2004/0093047 | A1 | 5/2004 | Lach |
| 2005/0049582 | A1 | 3/2005 | DeBenedictis et al. |
| 2005/0143719 | A1 * | 6/2005 | Sink .................... 606/9 |

OTHER PUBLICATIONS

Written Opinion for International Application No. PCT/IB05/01736, dated Jan. 31, 2006, 3 pages.

Anderson, R. R. and Ross, E. V., "Laser-Tissue Interactions." In: Fitzpatrick, R. E. and Goldman, M. P., editors, "Cosmetic Laser Surgery." Mosby, Inc., pp. 1-30.

* cited by examiner

DERMATOLOGICAL LASER SYSTEM AND METHOD FOR SKIN RESURFACING

CROSS REFERENCE TO RELATED APPLICATIONS

This application is a U.S. national stage filing of International Application No. PCT/IB2005/001736, filed Jun. 20, 2005, which claims priority to U.S. Provisional Application No. 60/686,907, filed Jun. 2, 2005 and U.S. Provisional Application No. 60/581,395, filed Jun. 21, 2004, each of which is hereby incorporated by reference herein in its entirety.

FIELD OF THE INVENTION

The present invention relates to laser pulse generation, and particularly to spatially and temporally shaped laser pulses, having pre-designed temporal shapes and two-dimensional 'random walk' spatial shapes, effective for skin resurfacing and dermatology in general, and the system for generating of these.

BACKGROUND OF THE INVENTION

Lasers have many useful applications to the treatment of surfaces, in the industrial field as well as in the medical field. Lasers have become valuable medical instruments to treat various kinds of dermatological conditions (e.g. a book edited by M. P. Goldman and R. E. Fitzpatrick entitled "Cutaneous Laser Surgery" published in 1999 by Mosby; or a book by R. E. Fitzpatrick and M. P. Goldman entitled "Cosmetic Laser Surgery" published in 2000 by Mosby). Current medical laser devices and methods include a laser system to generate a specific wavelength tailored to a particular dermatological application (See, e.g., U.S. Pat. No. 5,336,217 to Buys; U.S. Pat. No. 5,964,749 to Eckhouse; U.S. Pat. No. 6,120,497 to Anderson; or U.S. Pat. No. 6,273,885 to Koop). Or multi-color, multi-laser source, aimed at more applications in one multi-laser instrument (see e.g. U.S. Pat. No. 20040,082,940 to Black, Michael et al.).

Although the current devices and methods may work well for their intended purposes, they pose some drawbacks. For instance, with today's demand and wide variety of different dermatological applications, there is a strong desire to develop more versatile devices that can handle various kinds of dermatological applications rather than a single device tailored for a particular application, particularly if one can use the same laser, and change only the laser parameters, such as the temporal pulse shape, to serve the different needs. Furthermore, laser treatment may develop unwanted damage of non-targeted tissue, particularly the targeted tissue is subcutaneous. (For an overview of laser-tissue interaction, refer to, for instance, the paper by R. R. Anderson and E. V. Ross entitled "Laser-Tissue Interactions" in the book edited by R. E. Fitzpatrick and M. P. Goldman entitled "Cosmetic Laser Surgery," published in 2000 by Mosby, pp. 1-30). Some of the current devices and methods have attempted to overcome this negative effect by including a cooling device to cool down the non-targeted tissue (usually the skin) and thereby minimize the heat development and damage to that tissue (see, e.g. U.S. Pat. No. 5,964,749 to Eckhouse; U.S. Pat. No. 6,120,497 to Anderson; or U.S. Pat. No. 6,273,885 to Koop). However, such cooling devices add complexity and do not necessarily guarantee the anticipated cooling and reduced damage to non-targeted tissue, because the amount of cooling and the effect of the cooling device are unknown. Temporal pulse shaping may enable the reduction of total energy delivered to a spatial location, thus reducing the damage to non-targeted tissues and reducing or avoiding the need for active cooling.

Accordingly, there is a need to develop new dermatological devices and methods that provide versatility and flexibility. There is a further need to develop devices and methods that are not dependent on coolant devices and to minimize non-targeted tissue damage.

SUMMARY OF THE INVENTION

In one embodiment, the present invention is directed to a dermatological laser apparatus that may be used to treat a wide variety of problems, and conditions associated with the skin. This dermatological laser apparatus may comprise a laser light source having the ability to generate various temporal pulses in the same laser, where each pulse shape is optimized for a different treatment. The optimal temporal shape of the pulse is of importance when the processes occurring during the pulse are thermal or ablative and the pulse shape determines the temperature distribution and the spatial location of the ablated or heated tissue, in time and space, on the surface of, or within, the skin of a patient. Systems and methods for supplying high power, flexible, reconfigurable temporal laser pulse shaping for pulse durations of $10^{-10}$ to $10^{-2}$ seconds are provided.

In another embodiment, a dermatological laser system may be used to treat tissue, using a two-dimensional random walk, or other random processes, for the selection of treatment points that are addressed in a temporal sequence, one after another, by delivering a pulse or a train of pulses to one spatial point at one time point and switching to the next spatial point using a temporal and spatial switch. This two-dimensional random walk or random point selection has two added rules, executed by its software, controlling the switch. The first rule avoids the irradiation of an already treated point, by avoiding multiple irradiation of the same point. The second rule avoids the immediate surroundings of a just treated point when continuing to the next treated point, by not irradiating points adjacent a just treated point. Returning to treat the immediate surrounding, or the adjacent points of a just treated point, is executed after a time lag, in subsequent steps, thus allowing the treated point to cool down by conduction of heat to its cooler surrounding tissue. This method of delivery reduces the maximum laser power needed for the treatment, to the power needed for one point only, and enables the use of a low power laser as a treatment tool. More importantly, this method minimizes and reduces the heating of the adjacent or surrounding healthy tissues of the treated point, avoiding the problem of heat flow from many directions, that exists when a closely packed multiplicity of irradiated points are irradiated simultaneously. This method exposes the healthy tissue to less heat load, thus encouraging tissue re-growth. This method may eliminate the need for external cooling of the treated tissue One embodiment of the invention controls the spatial density of treated points, when using the two-dimensional random walk or random selection of treatment points, and allows selection of the maximum allowed number of points per unit area for a given treatment, by controlling the time and repetition rate, or the number of random steps, or points, per unit area. This also allows graceful reduction of spot concentration at the boundary of a treated area containing the spots, leading to a graceful, gradual, change from treated to non-treated area One specific embodiment of the invention uses an optical fiber delivery system to deliver the energy through a narrow neck in the external tissue, having dimensions similar to the fiber core size, thus leaving parts of the tissue totally undamaged to encourage tissue re-growth.

BRIEF DESCRIPTION OF THE DRAWINGS

Certain preferred embodiments of the invention will now be described with reference to the following illustrative figures. It is stressed that the particulars shown are by way of example and for purposes of illustrative discussion of certain embodiments of the present invention only.

In the drawings:

FIG. 2 is a graphic representation of a temporal pulse shape of;

DETAILED DESCRIPTION OF THE ILLUSTRATED EMBODIMENTS

Figure 1:
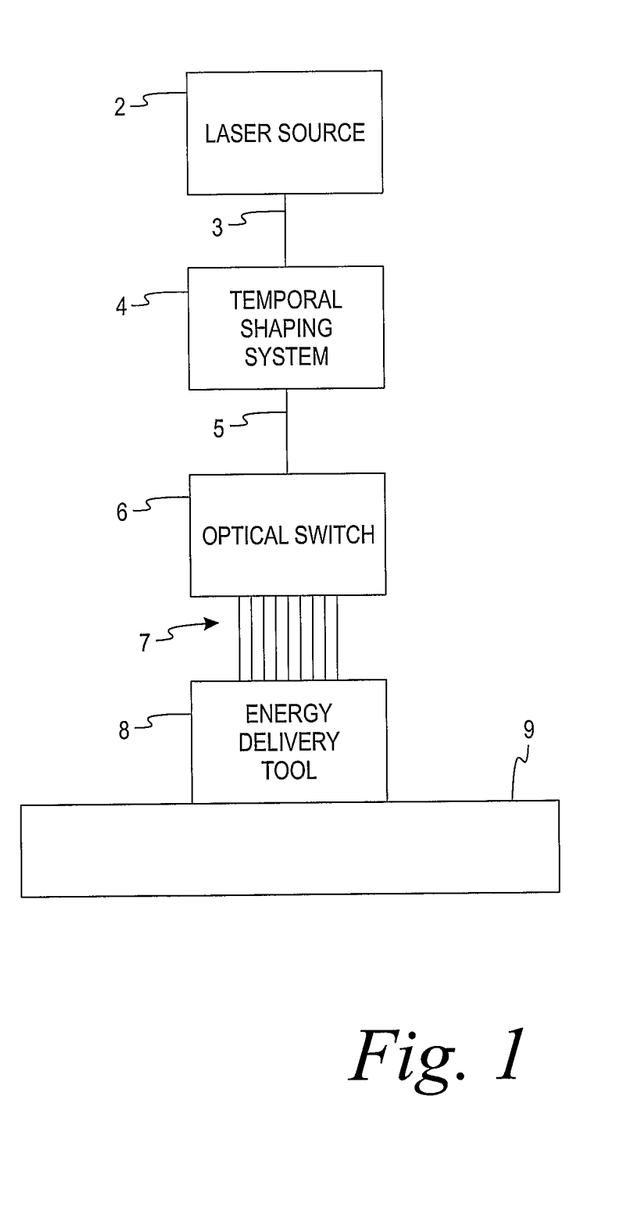
FIG. 1 is a block diagram of a dermatological laser system in accordance with one embodiment of the present invention.

Referring now to FIG. 1, a laser source 2, e.g., an Erbium-Glass laser, delivers a laser beam through an optical fiber 3 to a temporal shaping system 4 containing a flexible, reconfigurable, temporal laser pulse generating and shaping system. The laser pulse generating and shaping system can be any temporal shaper common in optics, such as a shutter, modulator or preferably a programmable optical pulse generator. The temporally shaped pulse is delivered 5 into an optical switch 6, where its power is transferred into one or more fibers in a multi-fiber conduit 7 (single or multi-mode fibers), which delivers the light into an energy delivery tool 8 that transmits the power into the patient's skin 9. The system consists of four major sub systems, namely, the laser source 2, the temporal shaping system or optical pulse generator 4, the optical switch 6 and the energy delivery tool 8.

One example of a suitable laser source 2 temporal shaping system 4 is described in copending application Serial No. PCT/IB2004/001889, filed Jun. 1, 2004 and entitled "Laser Pulse Generator," portions of which are set forth below in connection with FIGS. 7-9 of the drawings.

Figure 2:
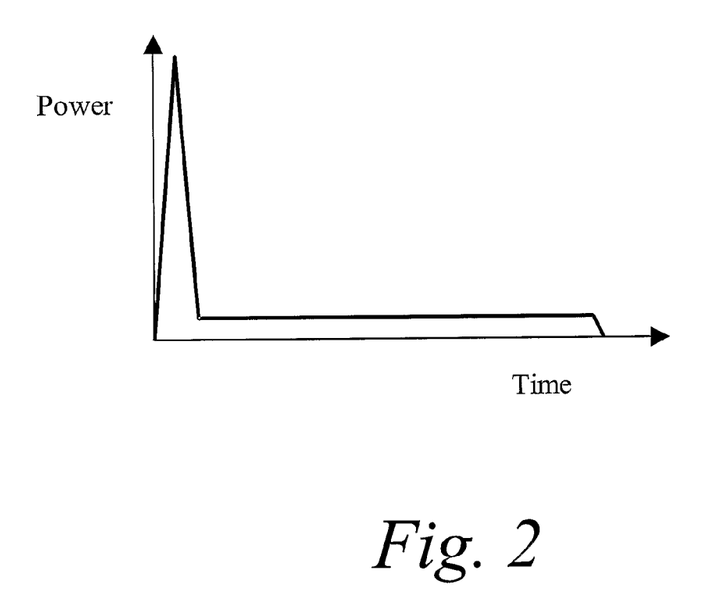

FIG. 2 is a graphic representation of a temporal pulse shape of an optimized pulse, e.g., for skin resurfacing, where the initial energy is high and the tail of the pulse is of low energy. The initial portion of the pulse is high enough to create non-linear absorption processes in the tissue, enabling the rest of the needed energy to be absorbed at low power and high absorption coefficient due to the preparation effected by the initial energy. The non-linear effect can be, e.g., excitation and absorption in the excited level, plasma formation or multi-photon absorption. The temporal pulse shape reduces the total energy needed for the process, thus minimizing or reducing heating of adjacent or surrounding tissues.

Figure 3A:
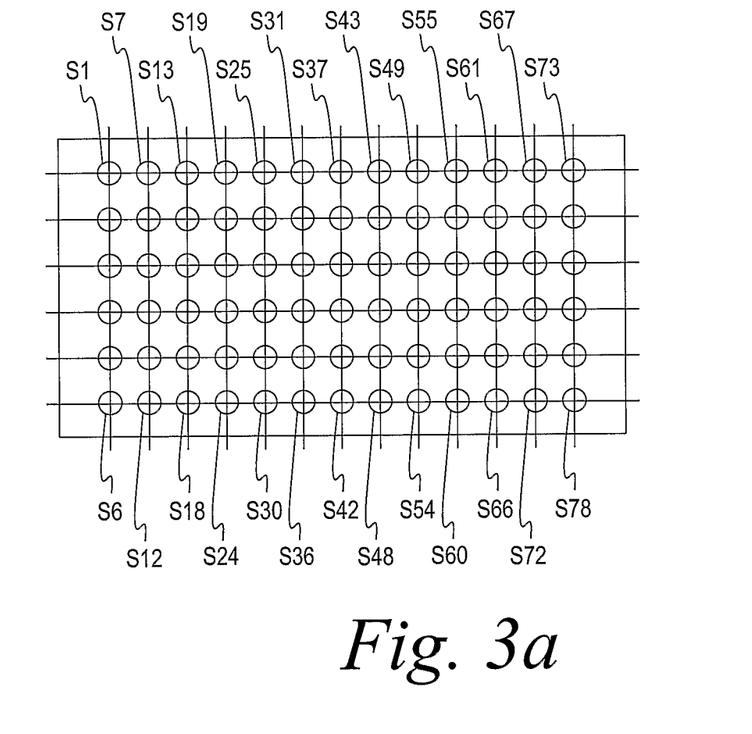
FIGS. 3a and 3b are schematic representations of a two-dimensional random walk
Figure 3B:
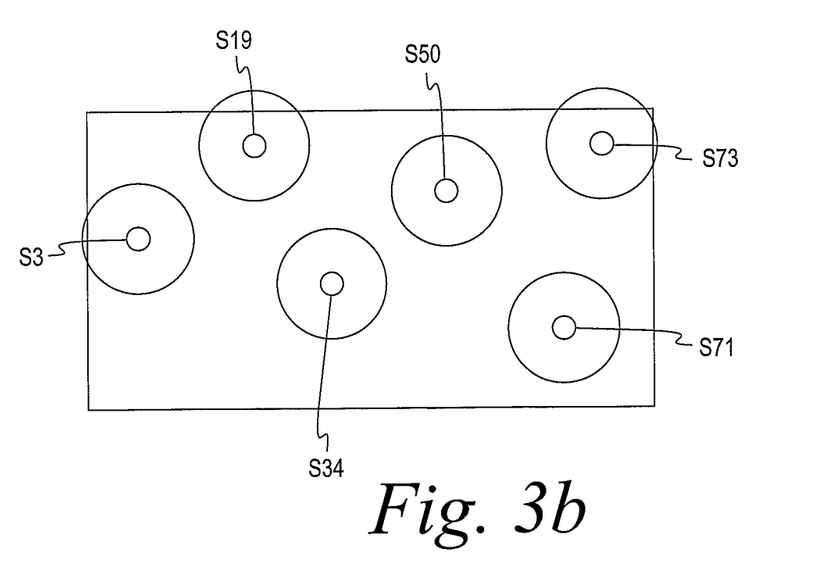

FIGS. 3a and 3b are schematic representations of the two-dimensional random walk. FIG. 3a illustrates an overall matrix of treatment points or sites S1 through S78, and FIG. 3b illustrates the first six sites that are irradiated in the order S3, S19, S34, S50, S73 and S-71. These treatment points are addressed in a temporal sequence, and spatially randomly, in a two-dimensional random walk, one after another, obeying the two additional rules stated previously. Treatment is executed by delivering a pulse or a train of pulses to the first spatial point S3 at one time point and then switching to the next spatial point S19 using the temporal and spatial switch of FIG. 1. As each site is irradiated, the laser pulse heat is dissipated in an adjacent area surrounding the irradiated site, such as the area S3' around the first site S3.

Figure 4:
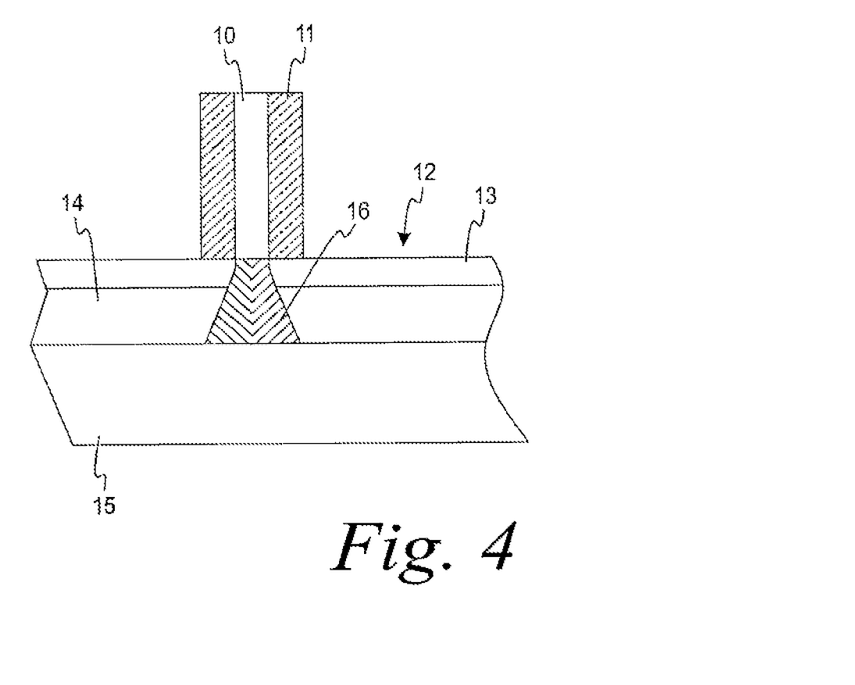
FIG. 4 is a schematic representation of an optimized energy delivery device.

FIG. 4 illustrates one embodiment of the energy delivery tool 8 shown in FIG. 1. Here the light comes through a fiber having a core 10 and a cladding 11, and is delivered directly to the patient's skin 12, where its passage through the thin (about 100 micrometers) epidermis 13 is narrow (e.g., 100 micrometers). The light beam then expands on its entry into the papillary dermis 14 where most of the absorption takes place, and only a small amount reaches the reticular dermis 15. The focused energy ablates a small epidermal volume at the upper part of a volume 16. A vapor bubble is formed in the transfer area of layers 13 and 14, opening a window to deeper tissue 15, and the defocused energy heats the papillary epidermis 15, destroying parts of it but leaving enough healthy tissue for fast regeneration.

Figure 5:
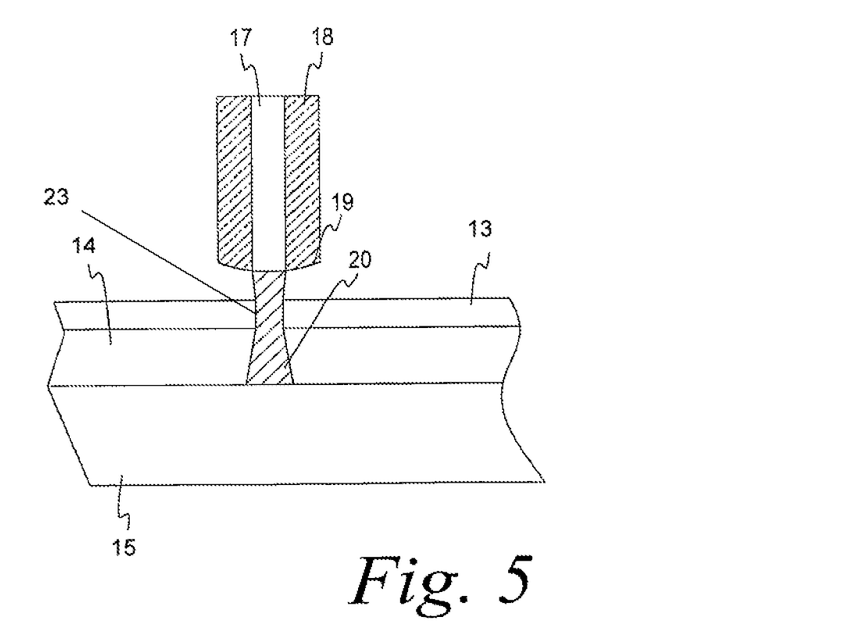
FIG. 5 is a schematic representation of an optimized energy delivery device having a lenticular end.

FIG. 5 illustrates a modified version of the energy delivery tool 8 shown in FIG. 1. Here the light comes through a fiber having a core 17 and a cladding 18, and passes through a lenticular-shaped fiber end 19, creating a small volume 20 as the treated volume. The process is identical to the process described above in connection with FIG. 4, but the shape of the treated volume can be changed by the lenticular-shaped end 19.

Figure 6:
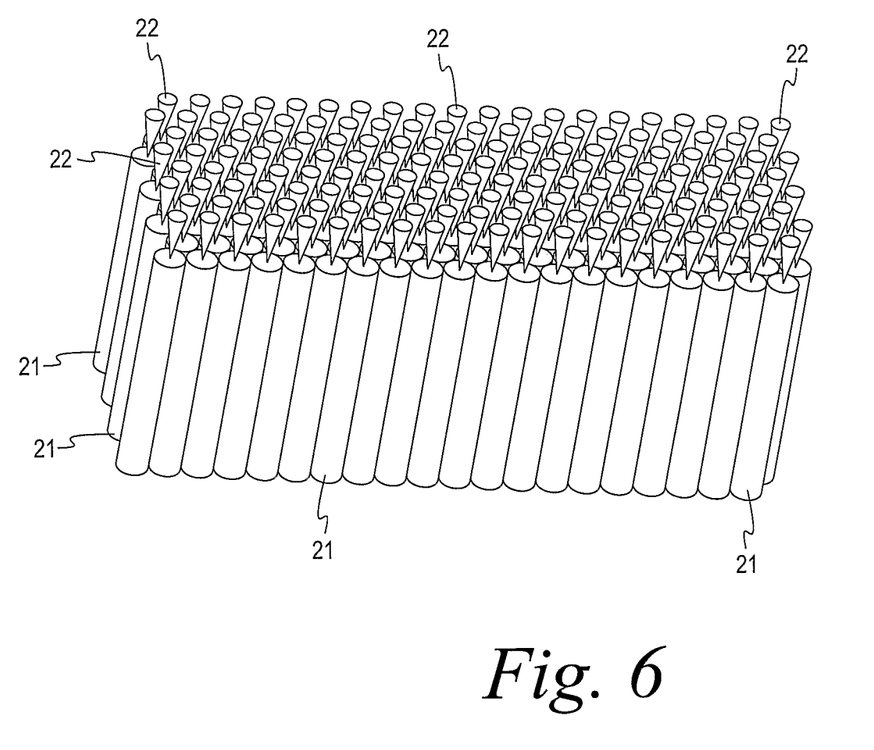
FIG. 6 is a schematic representation of an example of an energy delivery tool.

FIG. 6 illustrates an example of an array of basic units like these shown in FIGS. 4 and 5, where a two-dimensional array of fibers 21 can deliver temporally different optical beams 22 (each fiber at a different time), where the treated points are selected by the two-dimensional random walk or random point selection obeying the additional two rules as described before. The distance between adjacent fibers 21 can be as low as 50-125 microns, and the assembly can assume various fiber bundle geometries. The assembly may combine various sizes of fibers 21, or all the fibers may be of equal size. The step size for the random walk is preferably more than one fiber jump in a randomly selected direction.

Figure 7:
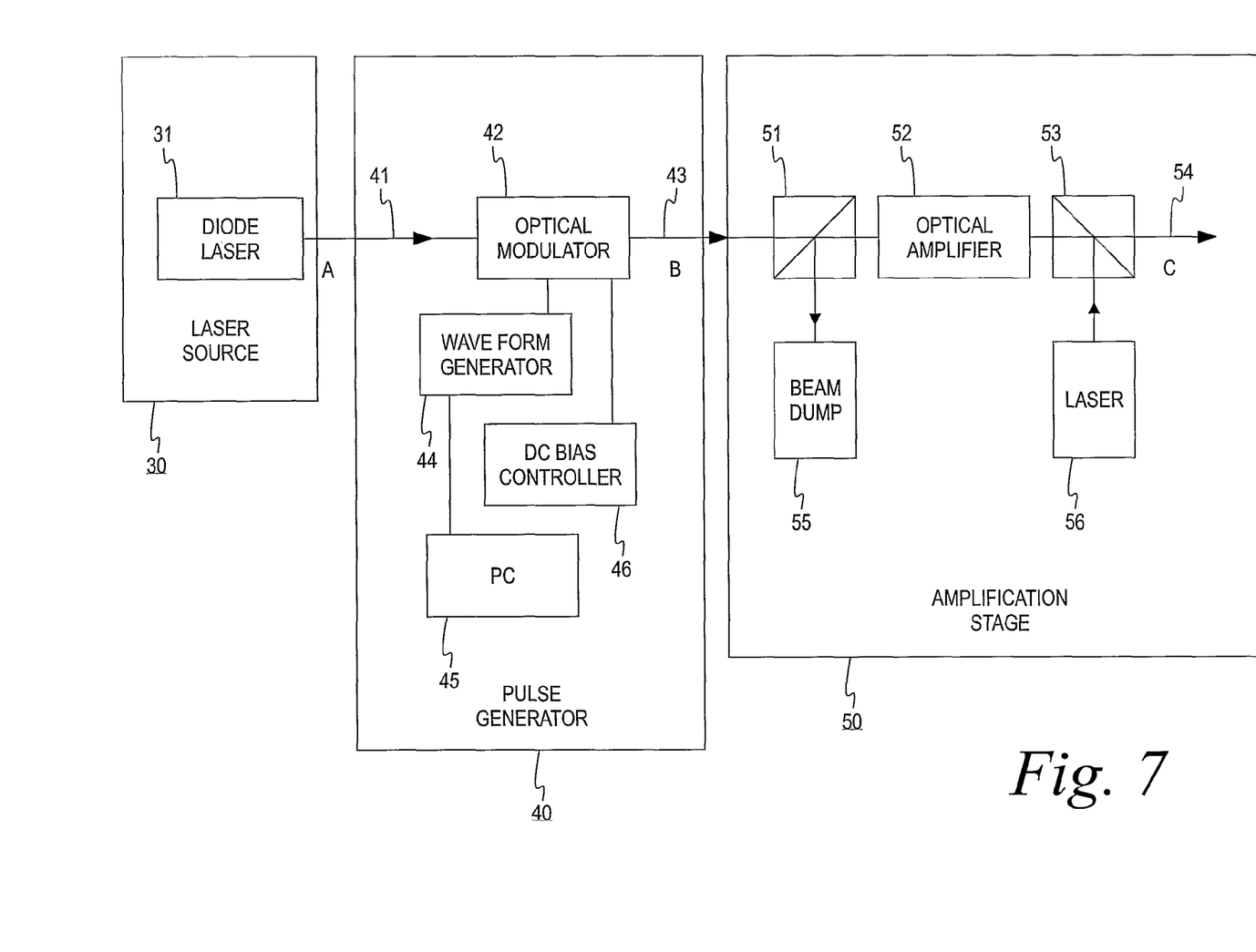
FIG. 7 is a schematic representation of a flexible, reconfigurable temporal laser pulse generating and shaping system.

Referring now to FIG. 7, there is shown a schematic representation of a flexible, reconfigurable temporal laser pulse generating and shaping system. The system consists of three major sub-systems, namely, a CW laser source 30, an optical pulse generator 40 and an amplification stage 50.

In one embodiment the flexible, reconfigurable temporal laser pulse shaper is based on a modulator, (e.g., a Mach-Zehnder (MZ) modulator) which is tuned to a non-common working point, the null state. In this case one can generate any shape of pulses with a desired power level (after amplification, up to more than 10 dB higher than the CW case). The time width of the pulse depends on the modulator's bandwidth. For example, using a 2.5 Gb/s MZ modulator, the time width of the pulses can vary from 500 ps to 100 µs, using other available modulators. As another example, using a 40 Gb/s operation enables the temporal shaping of pulses down to about 30 ps. The MZ modulator is electrically fed by an electrical pulse generator. Thus, optical pulses can be provided with any customized shape, depending on the pulse generator capability, or bandwidth, which is today commercially available at 40 Gb/s and higher.

In one embodiment, the amplifier amplifies within the 1500 nm wavelength range. Examples of amplifiers that may be used include an EDFA (Erbium Doped Fiber Amplifier), a Raman amplifier, or an SOA (Semiconductor Optical Amplifier). The first two are pumped by diodes and the third is directly pumped by electrical current. These devices work normally for amplifying CW or quasi CW lasers, but in this case are used to amplify pulses, and behave in a different way, as explained below. Special measures are taken to eliminate the ASE (Amplified Spontaneous Emission), which is a disturbing phenomenon, converting part of the inverted population energy into a noise-like radiation at the background level of the pulse.

The system can generate a variety of signals with different amplitude, frequency or pulse rate, rise time, fall time and delay time. The maximum output power of the pulse that can be generated can be more than 10 dB higher than the specification of the amplifier for CW input, due to the accumulation of inverted population at the laser level, in the amplifier.

The laser source 30 consists of, e.g., a fixed or tunable wavelength CW diode laser 31 of medium power, emitting polarized or non-polarized radiation into a fiber 41 at exit point A. While a diode laser has been shown in FIG. 7, it is to be understood that other types of laser sources can be used in specific embodiments of the present invention. In turn, the fiber 41 carries the light from the CW diode laser 31 to an optical modulator 42. In the case of polarized light, the fiber 41 will be a PM (Polarization Maintaining) fiber and the modulator will be a polarizing modulator (e.g., the Mach-Zehnder (MZ) modulator). In the case of non-polarized light, the fiber 41 will be a regular SMF fiber and the modulator will be an absorption modulator. In some embodiments, the wavelength can be any in the visible, near IR (Infra Red), e.g., 800 nm, 1300 nm or 1500 nm range, and can be, for example, a tunable laser with model number 3105/3106 manufactured by Agility Communications Inc, USA.

The optical pulse generator 40 consists of an optical modulator 42, such as an optical interferometric MZ modulator, fed by polarized laser light through the PM fiber 41 and emitting light through a fiber 43 at point B. The fiber 43 can be PM or non-PM fiber since the polarization is important only for the modulation by the MZ modulator phase. In one embodiment, a 10 Gb/s MZ modulator is used with a high extinction ratio (>20 dB) having a DC bias option. One example of a suitable modulator is a JDS Uniphase modulator, part no. 21023816, 10 Gb/s Amp. Modulator. A waveform generator 44 feeds the modulator 42 electrically; this arbitrary waveform generator 44 is capable of generating square, sine, triangle, exponential or any other desirable waveform. The waveform generator is supported by software to design the arbitrary wave, and can be controlled via, for example, a general purpose interface bus (GPIB) and RS232 protocols by a PC (Personal Computer) 45. In one embodiment, 50 MHz square-waves, namely, 100 MHz sampling rate pulses, may be generated using a pulse generator. One example of a suitable pulse generator is the 8085 Arbitrary Function Generator available from Tabor Electronics of Israel. To prevent or limit the working point of the modulators from drifting, and thus changing the shape of a generated pulse, an optional DC bias controller 46 may be used to keep the modulator 42 in the OFF state. The DC bias controller 46 inserts a very low modulation voltage into the bias port without affecting the shape of the signal. Such a technique is used in telecommunication systems, although they use different working points. A DC bias controller that has been used successfully in one embodiment is the P/N Micro-MBC-1 DC bias controller, which can be purchased from Pine Photonetics, USA. Light exiting the optical pulse generator 30 is guided into the amplification stage 50.

The laser source 30 and the optical pulse generator 40 can be combined into one unit of a self (direct) modulated laser, thus replacing the two units.

The amplification stage 50 is optically fed by the fiber 43 at point B through a splitter 51 into an optical amplifier 52. The light exits the amplification stage 50 through a splitter 53 into a fiber 54, exiting at point C. The optical amplifier 52 can be, for example, a diode pumped, fiber amplifier, a SOA or a solid state amplifier. Usually pulse amplifiers are designed to be free of ASE, but this is usually not the case with CW or quasi CW fiber amplifiers, and ASE suppression measures have to be taken. As an example of an ASE suppression means, one can use a very low intensity laser light source 56, having a wavelength inside the amplification range of the amplifier 52, which is homogenously broadened, but not the same as the wavelength of the laser 31, as a source for "cleaning" the spontaneous emission and creating a backward going beam, inserted into the amplifier 52 through the splitter or polarizer 53. The back-propagating beam is dumped at a beam dump 55 through a splitter or polarizer 51.

Figure 8:
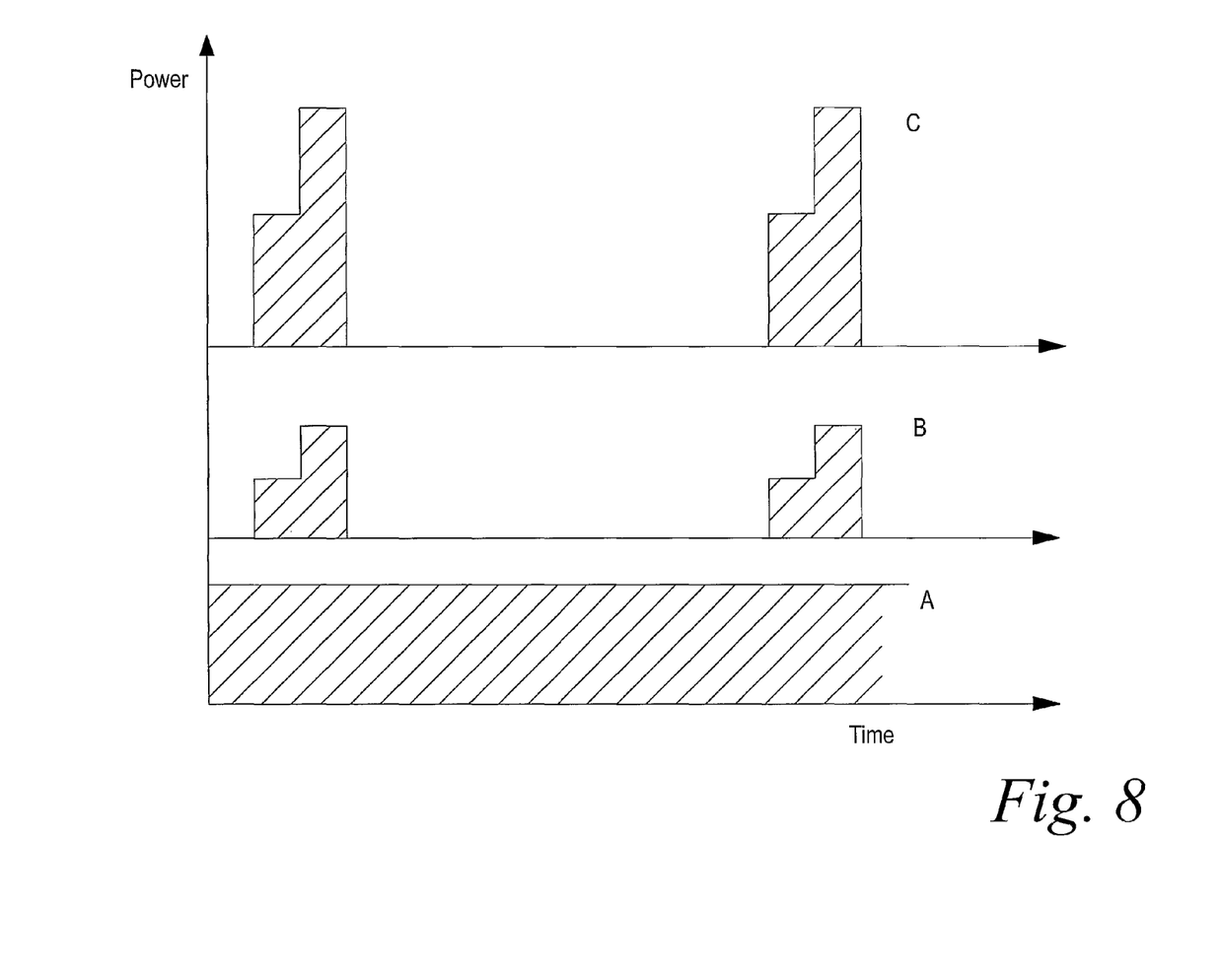
FIG. 8 is a graphic representation of pulse shapes at various points.

FIG. 8 is a graphic representation of pulse shapes at various points; here A is the CW low power shape at the exit of the laser, at point A of FIG. 7. Curve B shows the modulated light after passing through the fast modulator, where the modulator can assume various shapes, and here only a simple example is given, measured at point B of FIG. 7. Curve C is the amplified version, measured after the amplifier, at point C of FIG. 7.

Figure 9:
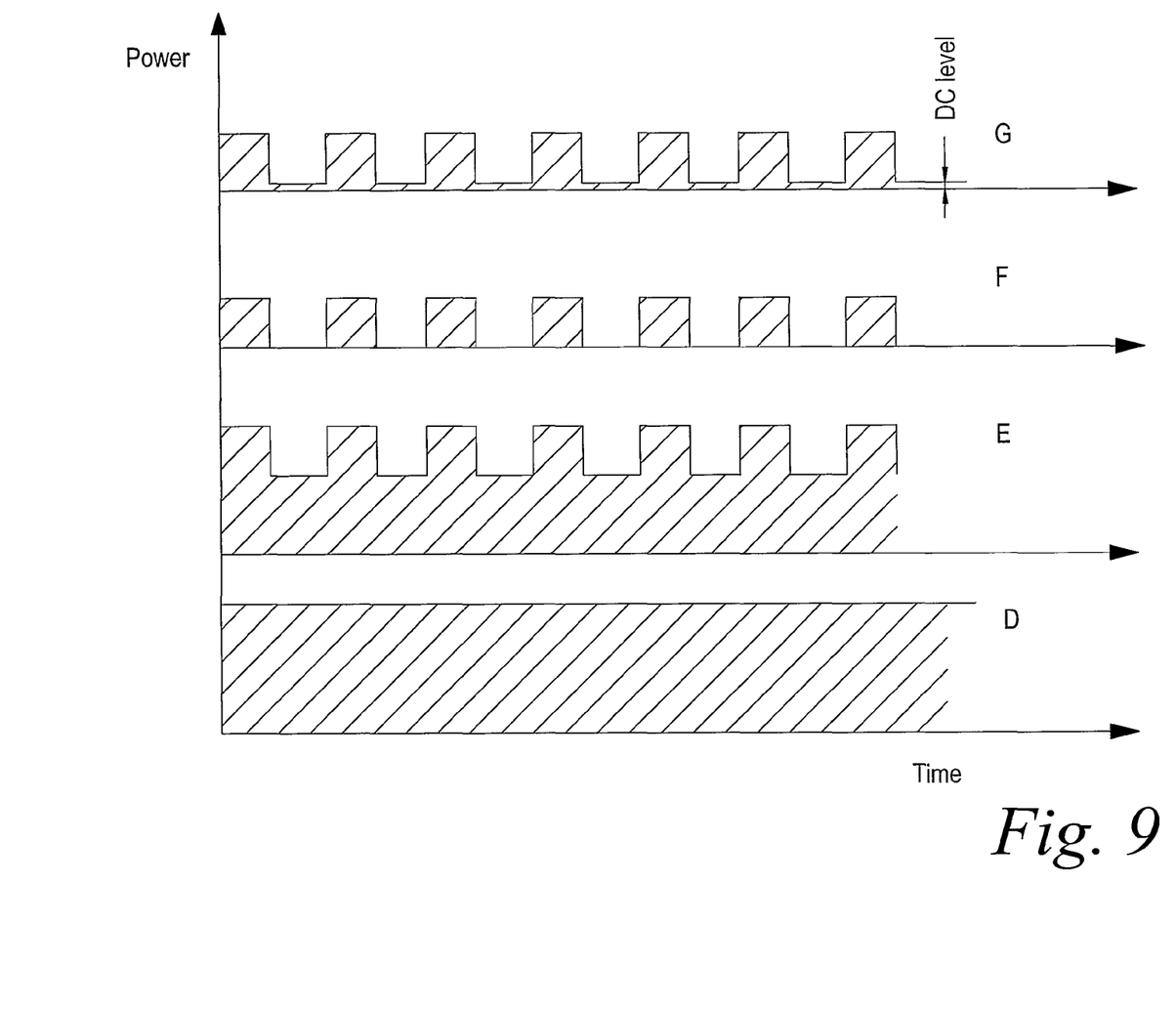
FIG. 9 is a graphic illustration of the null point operation of the MZ modulator.

FIG. 9 is a graphic representation of the null point operation of the MZ modulator. Here, all the curves are measured at point B of FIG. 7. The curve D represents an always open MZ modulator. Curve E represents the regular way of modulation, having a large DC level with pulses on its top. Curve F represents the "clean," without DC level pulses, where the DC bias controller is used to shift the operation point of the MZ modulator. Curve G shows (not to scale) the feedback loop control of the DC bias controller, having a small, negligible DC level.

Systems and methods according to the present invention may be incorporated into a number of skin treatments, such as skin resurfacing.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of irradiating human tissue with light, comprising
   sequentially irradiating each of a multiplicity of sites on said tissue,
   successive sites being selected to (a) avoid the irradiation of a site previously irradiated in the current treatment, to avoid multiple irradiations of the same site in the same treatment, and (b) avoid the irradiation of any site adjacent a site just irradiated by the preceding irradiation,
   with at least one optical pulse having a temporal shape that varies in amplitude from a leading peak that is shaped temporally to initiate non-linear absorption by the skin tissue, to a tail with a lower amplitude, and is selected for a predetermined dermatological treatment from multiple temporal pulse shapes for different dermatological treatments, said multiple temporal pulse shapes varying in amplitude.

2. The method of claim 1 wherein said at least one optical pulse comprises a train of optical pulses.

3. The method of claim 1 wherein said optical pulse is applied to said tissue through an optical fiber.

4. The method of claim 3 wherein said optical fiber is part of an array of optical fibers that sequentially receive optical pulses for application to said tissue.

5. The method of claim 1 wherein the temporal shape of said optical pulse is varied for different treatments of said tissue.

6. The method of claim 1 wherein said multiplicity of sites are irradiated sequentially by a two-dimensional random-walk process.

7. The method of claim 1 wherein said multiplicity of sites are irradiated sequentially by a two-dimensional random point selection process.

8. The method of claim 1 wherein each of said multiplicity of sites is irradiated only once.

9. The method of claim 1 wherein said multiplicity of sites are irradiated one at a time.

10. The method of claim 1 wherein said sequential irradiation of said multiplicity of sites is controlled by a temporal switch.

11. A method of irradiating human tissue with light, comprising sequentially irradiating each of a multiplicity of sites on said tissue with at least one optical pulse having a temporal shape that is selected for a predetermined dermatological treatment from multiple temporal pulse shapes for different dermatological treatments, said different temporal pulse shapes including pulse shapes that vary in amplitude, wherein said optical pulse is applied to said tissue through an optical fiber, and wherein said optical pulse is delivered to said tissue through a narrow neck at the end of said fiber so that the tissue surrounding said narrow neck is undamaged to encourage tissue re-growth.

* * * * *